US009737313B1

(12) United States Patent
Sohn et al.

(10) Patent No.: US 9,737,313 B1
(45) Date of Patent: Aug. 22, 2017

(54) SHOULDER REAMER DEVICES, SYSTEMS INCLUDING THE SAME, AND RELATED METHODS

(71) Applicant: Roger C. Sohn, San Clemente, CA (US)

(72) Inventors: Roger C. Sohn, San Clemente, CA (US); Shawn J. Collins, Sammamish, WA (US)

(73) Assignee: Roger C. Sohn, San Clemente, CA (US)

( * ) Notice: Subject to any disclaimer, the term of this patent is extended or adjusted under 35 U.S.C. 154(b) by 0 days.

(21) Appl. No.: 15/345,337

(22) Filed: Nov. 7, 2016

(51) Int. Cl.
A61B 17/16 (2006.01)

(52) U.S. Cl.
CPC ...... A61B 17/1615 (2013.01); A61B 17/1684 (2013.01)

(58) Field of Classification Search
CPC ............ A61B 17/1615; A61B 17/1666; A61B 17/1684
See application file for complete search history.

(56) References Cited

U.S. PATENT DOCUMENTS

| 6,783,533 | B2 | 8/2004 | Green et al. |
| 8,241,289 | B2 | 8/2012 | Maisonneuve |
| 8,246,621 | B2 | 8/2012 | Poncet |
| 8,357,163 | B2 | 1/2013 | Sidebotham et al. |
| 8,523,867 | B2 | 9/2013 | Rauscher et al. |
| 2003/0097133 | A1 | 5/2003 | Green et al. |
| 2004/0236339 | A1 | 11/2004 | Pepper |
| 2005/0113836 | A1 | 5/2005 | Lozier et al. |
| 2007/0005074 | A1 | 1/2007 | Chudik |
| 2009/0270863 | A1 | 10/2009 | Maisonneuve |
| 2009/0270867 | A1 | 10/2009 | Poncet |

(Continued)

FOREIGN PATENT DOCUMENTS

| EP | 2623050 | 8/2013 |
| EP | 2666418 | 11/2013 |

(Continued)

OTHER PUBLICATIONS

English-language machine translation of European Patent No. 2666418, Nov. 27, 2013.

(Continued)

Primary Examiner — David Bates
Assistant Examiner — Olivia C Chang
(74) Attorney, Agent, or Firm — Dascenzo Intellectual Property Law, P.C.

(57) ABSTRACT

Presently disclosed reamer devices include a longitudinally-extending slot formed through a cutter head portion and a portion of a shaft, thereby allowing engagement of the reamer device with a guide pin inserted into a patient's glenoid by passing the guide pin through the slot and into an interior cannula track extending longitudinally through the interior of the shaft and cutter head portion. Presently disclosed reamer devices may be configured to engage the guide pin when the cutter head portion is positioned at a location medial to the patient's humeral head. Presently disclosed systems include such reamer devices and a guide pin, such as a dual diameter guide pin having an enlarged portion and a smaller portion. Dual diameter guide pins may interact with the interior cannula track of the shaft of the reamer device to serve as a depth limit for advancement of the reamer device along the guide pin.

20 Claims, 6 Drawing Sheets

(56) References Cited

U.S. PATENT DOCUMENTS

| | | |
|---|---|---|
| 2010/0063507 A1 | 3/2010 | Sidebotham et al. |
| 2012/0123419 A1 | 5/2012 | Purdy et al. |
| 2013/0110116 A1 | 5/2013 | Kehres et al. |
| 2013/0150859 A1 | 6/2013 | Kehres et al. |
| 2015/0073417 A1 | 3/2015 | Norton et al. |
| 2015/0073424 A1 | 3/2015 | Couture et al. |
| 2015/0190147 A1 | 7/2015 | Ferragamo et al. |
| 2015/0320430 A1 | 11/2015 | Kehres et al. |
| 2015/0342620 A1 | 12/2015 | Winslow |
| 2015/0342622 A1 | 12/2015 | Kehres et al. |
| 2015/0374502 A1 | 12/2015 | Hodorek et al. |

FOREIGN PATENT DOCUMENTS

| | | |
|---|---|---|
| GB | 2406278 | 3/2005 |
| WO | 2009/083707 | 7/2009 |
| WO | 2014/089198 | 6/2014 |

OTHER PUBLICATIONS

Zimmer, Bigliani/Flatow®: The Complete Shoulder Solution Cannulated Instruments, product information and surgical technique guide, 2009.

Biomet, Comprehensive Reverse Shoulder System, product information and surgical technique guide, 2011.

Biomet, Signature Personalized Patient Care for Comprehensive Total and Reverse Shoulder Systems, product information and surgical technique guide, 2013.

Biomet, Comprehensive Total Shoulder System Featuring Comprehensive Access Glenoid Instrumentation, product information and surgical technique guide, 2014.

DePuy Synthes Joint Reconstruction, Global APG+ (Anchor Peg Glenoid) Product Rationale & Surgical Technique, product information and surgical technique guide, Apr. 2014.

Exatech®, Equinoxe® Platform Shoulder System, product information and surgical technique guide, 2015.

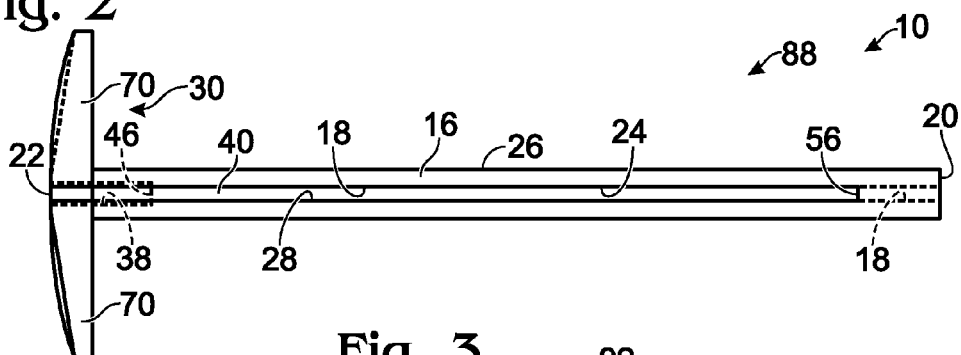
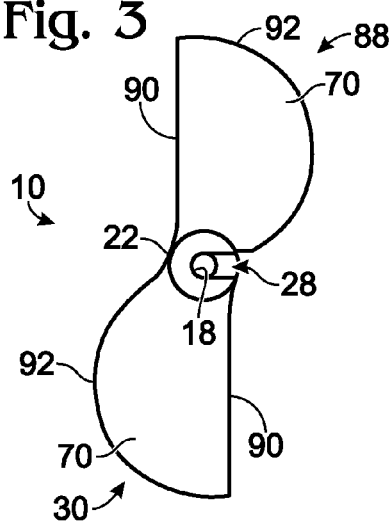
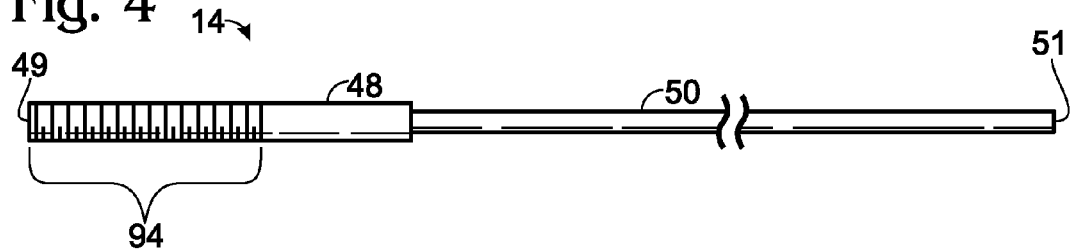
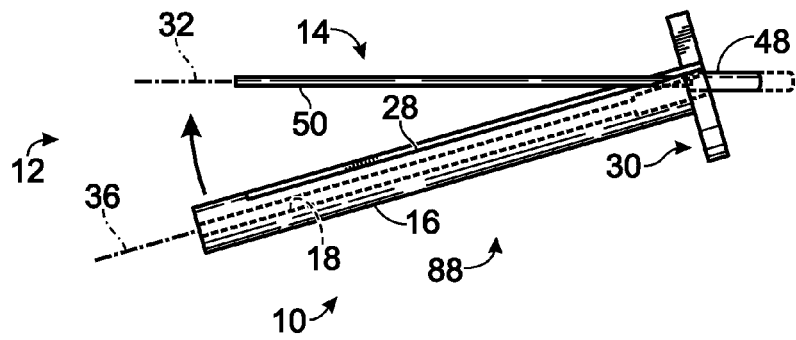

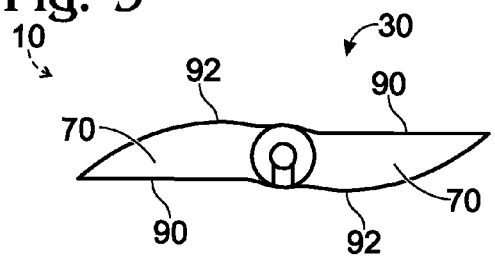
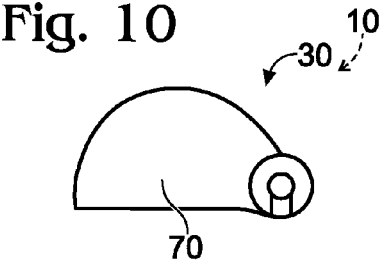
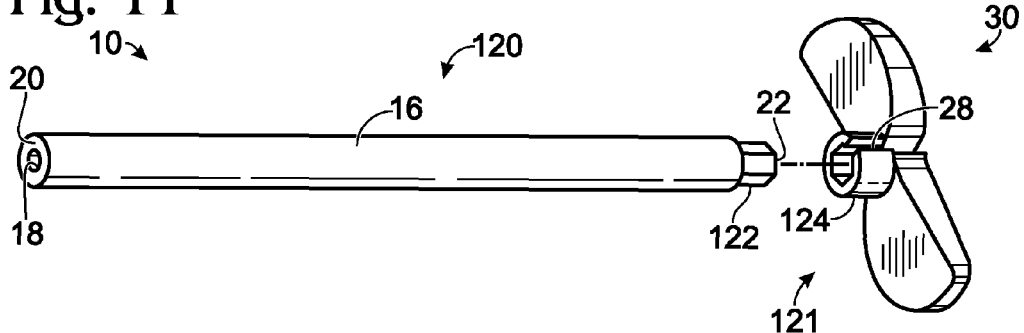
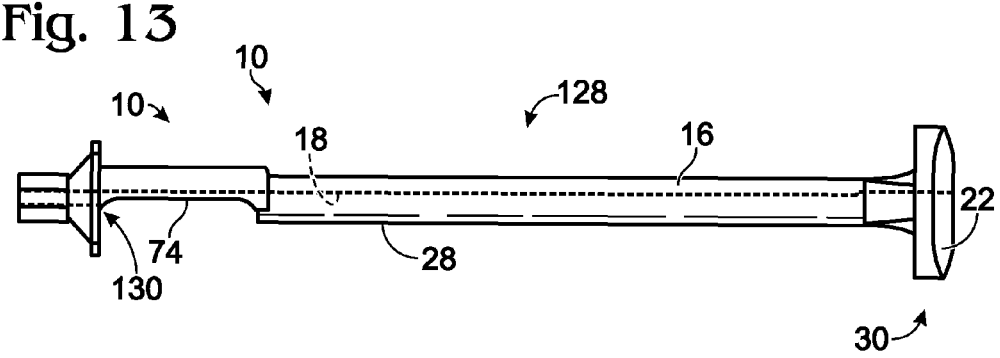
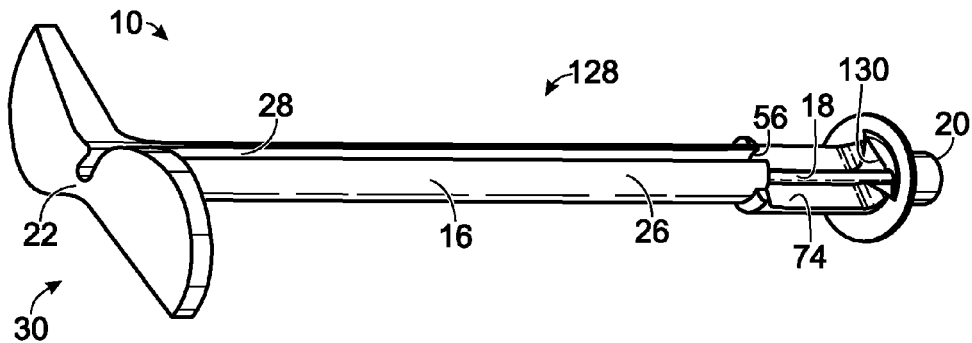

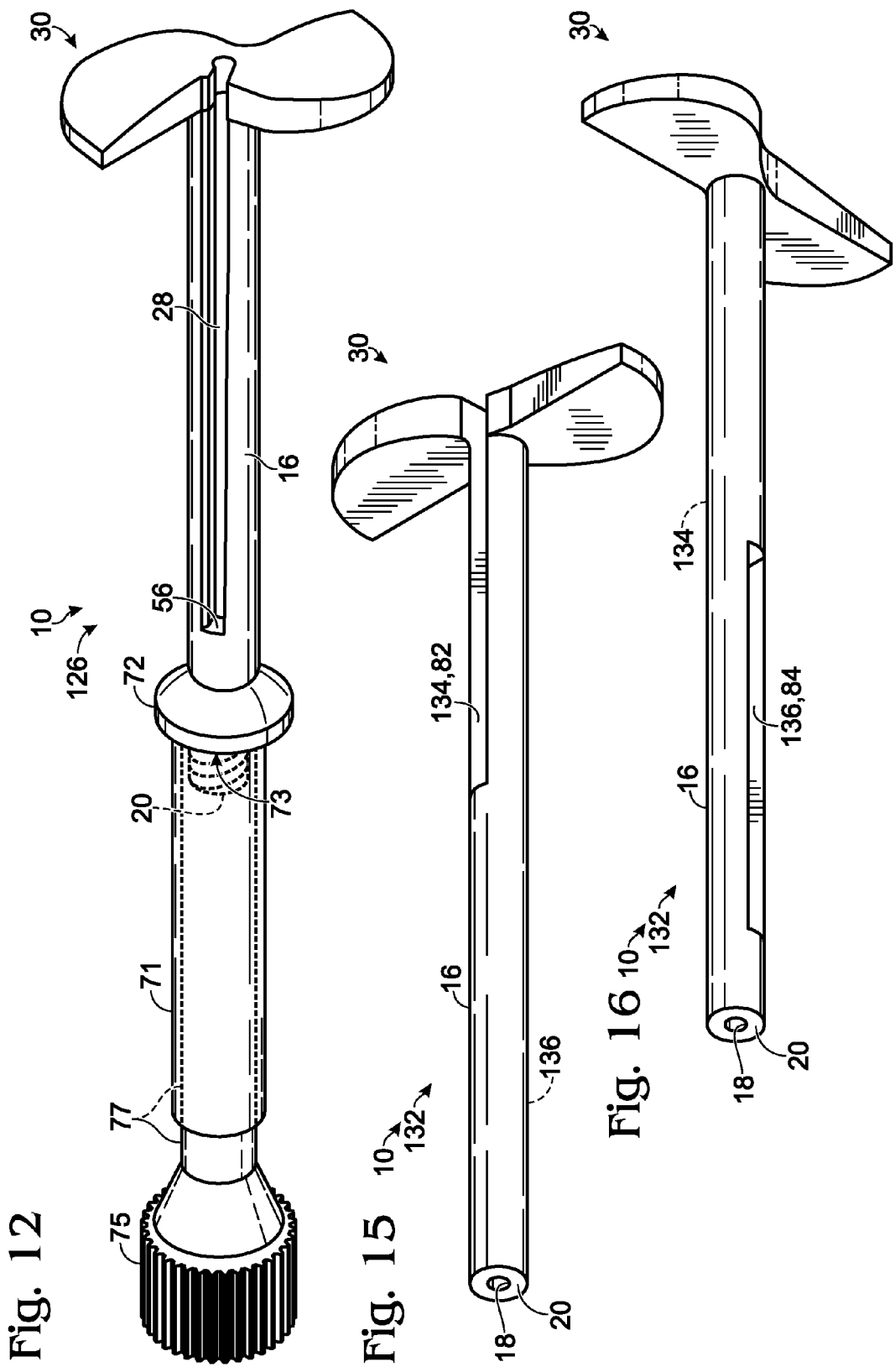

SHOULDER REAMER DEVICES, SYSTEMS INCLUDING THE SAME, AND RELATED METHODS

FIELD

The present disclosure relates to shoulder arthroplasty.

BACKGROUND

Shoulder replacement surgery (referred to medically as "shoulder arthroplasty," or "total shoulder arthroplasty") involves removal of a portion of the glenoid surface (the socket portion of the ball-and-socket shoulder joint), performed by a reamer (or "reaming device"). Reamers generally consist of one or more spinning blades that remove bone from the glenoid surface. Such reamers generally are cannulated, such that they are inserted over a guide wire and/or guide pin, to the location of the reaming. After the glenoid surface is so prepared, a glenoid component of a prosthetic shoulder joint is placed. A portion of the patient's humerus also may be replaced in such procedures. The depth of the wound created while reaming the glenoid surface and the tension of surrounding soft tissues make it difficult to see landmarks accurately, often making glenoid preparation the most challenging step. Additionally, the humeral head (the ball portion of the shoulder joint, that fits into the glenoid) often interferes with the reamer's access to the glenoid, and the reamer can damage the humeral head and surrounding soft tissues as the reamer is inserted past the humeral head and then subsequently removed after reaming the glenoid.

Total shoulder arthroplasty has undergone significant refinement in the last decade. Advances in implants and instruments designed to aid the insertion of implants have greatly improved the accuracy and efficiency of the operation. Even so, prior attempts at minimizing damage to the humeral head and surrounding tissues each come with significant disadvantages. For example, such techniques have involved forgoing the use of the guide pin (which reduces accuracy of the procedure), bending the guide pin while advancing the reamer past the humeral head (which may deform and/or break the guide pin, resulting in inaccurate reaming and/or a broken guide pin), and/or modifying the reamer, such as by cutting out a portion of the circular reamer head, for example to create a "bowtie" or "propeller" shape, to make advancement past the humeral head easier. Despite these improvements, insertion of the glenoid reamer is still often difficult and potentially traumatic to the soft tissues or bony structures such as the deltoid muscle, strap muscles, and the lesser tuberosity.

SUMMARY

Presently disclosed shoulder reamer devices include a shaft extending from a proximal end to a distal end, and a cutter head portion positioned at the distal end of the shaft. The shaft includes an inner surface defining an interior cannula track, and the shaft is configured to receive a guide pin within the interior cannula track such that the guide pin is substantially parallel with the interior cannula track when received in the interior cannula track. The shaft also includes an outer surface opposite the inner surface, with a slot formed in the outer surface. The slot extends longitudinally along the shaft from the distal end of the shaft towards the proximal end of the shaft, and it extends radially from the outer surface of the shaft to the interior cannula track. The cutter head portion is configured to cut a patient's bone in preparation for receiving an implant component, and the interior cannula track and slot extend through the cutter head portion. Presently disclosed reamer devices may be configured to allow for engagement of the reamer device with the guide pin at a later point in the reaming procedure than do prior art reaming devices. In this manner, presently disclosed reamer devices may advantageously lessen potential damage to the humeral head and surrounding tissues when performing a shoulder arthroplasty or related procedures.

Presently disclosed methods include inserting a guide pin into a patient's glenoid, providing a reamer device according to the present disclosure, and engaging the reamer device with the guide pin at a location medial to the patient's humeral head by moving the shaft with respect to the guide pin such that the guide pin passes radially through the slot formed in the shaft, and such that the guide pin is received within the inner cannula track of the shaft. Methods further include capturing the guide pin within the shaft, which may be performed automatically due to the configuration of the reamer device, or may be performed by a separate step, such as positioning a sliding ring on the shaft to capture the guide pin within the shaft.

BRIEF DESCRIPTION OF THE DRAWINGS

FIG. 2 is a side elevation view of one example of a reamer device according to the present disclosure.

FIG. 3 is a top plan view of the reamer device of FIG. 2.

FIG. 4 is a side elevation view of a guide pin for use with the reamer devices of the present disclosure.

FIG. 5 is a top plan view of one example of a reamer device being positioned onto a guide pin inserted in a patient's bone, according to the present disclosure.

FIG. 9 is a top plan view of another example of a reamer device according to the present disclosure.

FIG. 10 is a top plan view of another example of a reamer device according to the present disclosure.

FIG. 11 is a side elevation view of another example of a reamer device according to the present disclosure.

FIG. 12 is a perspective view of another example of a reamer device according to the present disclosure.

FIG. 13 is a side elevation view of another example of a reamer device according to the present disclosure.

FIG. 14 is a close-up perspective view of a portion of the reamer device of FIG. 13.

FIG. 15 is a perspective view of an example of a reamer device having two slots according to the present disclosure, viewed from the right.

FIG. 16 is a perspective view of the reamer device of FIG. 15, viewed from the left.

DESCRIPTION

Figure 1:
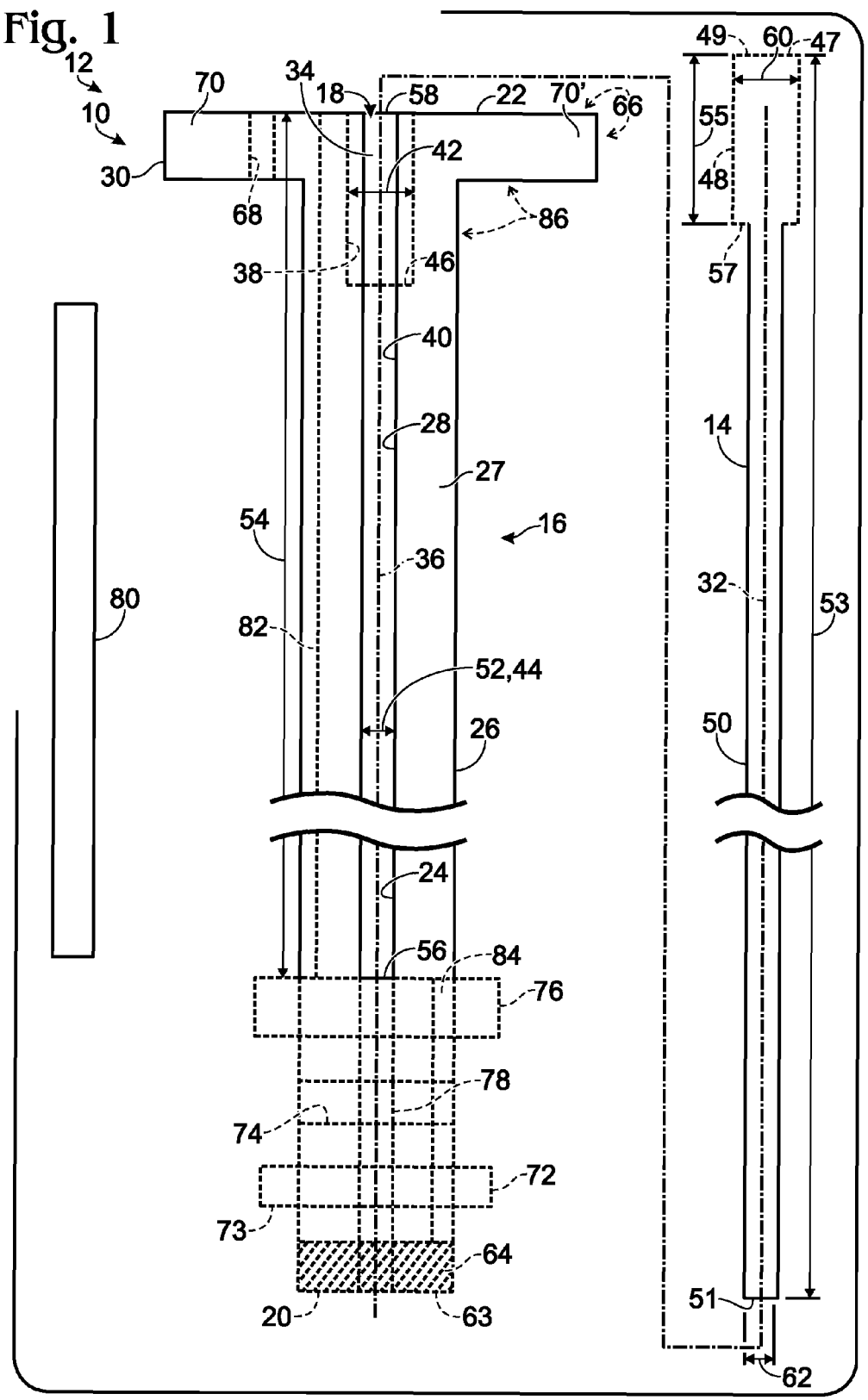
FIG. 1 is a schematic representation of examples of reamer devices and systems according to the present disclosure.

FIGS. 1-14 provide examples of reamer devices 10, systems 12, and/or guide pins 14 according to the present disclosure. Elements that serve a similar, or at least substantially similar, purpose are labeled with like numbers in each of FIGS. 1-14, and these elements may not be discussed in detail herein with reference to each of FIGS. 1-14. Similarly, all elements may not be labeled in each of FIGS. 1-14, but reference numerals associated therewith may be utilized herein for consistency. Elements, components, and/or features that are discussed herein with reference to one or more of FIGS. 1-14 may be included in and/or utilized with any of FIGS. 1-14 without departing from the scope of the present disclosure.

FIG. 1 schematically illustrates systems 12 according to the present disclosure, which generally include a reamer device 10 and a guide pin 14. Reamer device 10 (which may also be referred to as a mill, a cutter, a reaming device, or a burr) is configured to engage guide pin 14 in order to perform a reaming operation on a patient's bone. Reamer devices 10 are generally described as used in performing a shoulder arthroplasty, but reamer devices 10 of the present disclosure may be configured or adapted for performing reaming operations on other bone surfaces within a patient as well. Generally, guide pin 14 is inserted into the patient's bone, at which point reamer device 10 may be engaged with guide pin 14 such that guide pin 14 is positioned within a shaft 16 of reamer device 10 (e.g., guide pin 14 is partially received within an interior cannula track 18 of reamer device 10). Then, reamer device 10 may be used to cut (e.g., ream, drill, mill, slice, etc.) the patient's bone in which guide pin 14 is inserted.

Shaft 16 extends from a proximal end 20 to a distal end 22. Interior cannula track 18 extends longitudinally within shaft 16 from proximal end 20 to distal end 22, and reamer device 10 is configured such that guide pin 14 is substantially parallel to and coaxial with interior cannula track 18 when received therein. Interior cannula track 18 is defined by an inner surface 24 of shaft 16, and shaft 16 also includes an outer surface 26 opposite inner surface 24. Shaft 16 also includes a slot 28 formed in outer surface 26 and extending longitudinally along shaft 16 from distal end 22 towards proximal end 20. Slot 28 extends radially inward from outer surface 26 to interior cannula track 18. In other words, slot 28 is formed through the entire thickness of a wall 27 of shaft 16, from outer surface 26 to inner surface 24. In use, guide pin 14 may be inserted into interior cannula track 18 by passing guide pin 14 through slot 28, as will be described in more detail below.

A cutter head portion 30, positioned at distal end 22 of shaft 16, is configured to cut a patient's bone in preparation for receiving an implant component during surgery (e.g., in the course of shoulder arthroplasty). For example, reamer device 10 may be configured to prepare a patient's glenoid for shoulder arthroplasty, such as by cutting the glenoid surface using cutter head portion 30, thereby preparing the glenoid to receive a prosthetic glenoid component.

Shaft 16 is configured to slide longitudinally with respect to guide pin 14 once reamer device 10 has been engaged with guide pin 14. In other words, interior cannula track 18 is sized and shaped with respect to guide pin 14 such that guide pin 14 may be received within interior cannula track 18 and such that shaft 16 may be selectively moved with respect to guide pin 14 once guide pin 14 is so received. In this manner, guide pin 14 may be inserted into a patient's bone to provide alignment and positioning guidance, and reamer device 10 may be engaged with guide pin 14, and then advanced longitudinally along guide pin 14 towards the patient's bone surface.

Guide pin 14 generally extends from a leading end 49 to a trailing end 51, with leading end 49 being configured to be inserted partially into the patient's bone (e.g., the patient's glenoid) that the reamer device is configured to cut. Guide pin 14 is configured to assist in alignment and positioning of reamer device 10 with respect to the patient's bone. Guide pin 14 may include an enlarged guide pin portion 48 and a smaller guide pin potion 50 in some examples. In such examples, a first diameter of enlarged guide pin portion 48 is larger than a second diameter of smaller guide pin portion 50. In some examples, leading end 49 of guide pin 14 includes a cutting point 47 configured for cutting into the patient's bone, such as a drill tip or a four-sided tip, that is used to drill into the patient's bone as guide pin 14 is inserted.

Reamer device 10 is configured to be placed onto guide pin 14 by non-longitudinal (e.g., lateral and/or posterior) movement of shaft 16 with respect to guide pin 14 (reamer device 10 also may be configured to allow conventional, longitudinal placement onto guide pin 14). In other words, movement of shaft 16 in a direction that is at an angle to (e.g., transverse to, and in some cases orthogonal to) a longitudinal axis 32 of guide pin 14, such that guide pin 14 passes through slot 28, causes guide pin 14 to be received into interior cannula track 18. In this manner, shaft 16 is configured to engage guide pin 14 by moving shaft 16 relative to guide pin 14 such that at least a portion 34 of slot 28 formed in cutter head portion 30 moves towards guide pin 14. In some examples, reamer device 10 is configured to engage guide pin 14 by pivoting shaft 16 with respect to guide pin 14 such that cutter head portion 30 moves towards guide pin 14.

In one specific example, shaft 16 is configured to engage guide pin 14 by placing cutter head portion 30 in proximity to guide pin 14 such that shaft 16 is positioned at a non-parallel angle with respect to guide pin 14 (e.g., such that a longitudinal axis 36 of shaft 16 is non-parallel with longitudinal axis 32 of guide pin 14), radially aligning shaft 16 with guide pin 14 such that slot 28 faces guide pin 14, moving cutter head portion 30 towards guide pin 14 such that portion 34 of slot 28 formed in cutter head portion 30 is placed onto guide pin 14, and then pivoting shaft 16 towards guide pin 14 until guide pin 14 and shaft 16 are substantially parallel (e.g., until longitudinal axis 32 is substantially parallel to and coaxial with longitudinal axis 36) and guide pin 14 passes through slot 28 and is received within interior cannula track 18.

In some examples, interior cannula track 18 includes an enlarged inner diameter portion 38 and a reduced inner diameter portion 40, with enlarged inner diameter portion 38 having an enlarged inner diameter 42 that is greater than a reduced inner diameter 44 of reduced inner diameter portion 40. Enlarged inner diameter portion 38 is positioned distal to reduced inner diameter portion 40. As used herein, a first feature is "distal to" a second feature when the first feature is positioned closer to distal end 22 than is the second feature. In some examples, enlarged inner diameter portion 38 is adjacent cutter head portion 30, such as extending through cutter head portion 30 as shown in FIG. 1 (e.g., the portion of interior cannula track 18 that is positioned through cutter head portion 30 may form at least a portion of enlarged inner diameter portion 38). In other words, enlarged inner diameter portion 38 may extend longitudinally from distal end 22 of shaft 16 towards proximal end 20 of shaft 16.

Enlarged inner diameter portion 38 and reduced inner diameter portion 40 may be immediately adjacent one another such that interior cannula track 18 is a single, continuous cannula track. Enlarged inner diameter portion 38 and reduced inner diameter portion 40 are generally coaxial, but this need not necessarily be the case. Interior cannula track 18 may include a step 46 at the interface of enlarged inner diameter portion 38 and reduced inner diameter portion 40. Step 46 may be configured to engage guide pin 14. For example, guide pin 14 may be a dual diameter guide pin, having enlarged guide pin portion 48 and smaller guide pin portion 50, and step 46 may engage enlarged guide pin portion 48. In this manner, step 46 and such a dual diameter guide pin 14 may function together as a depth limit, such that reamer device 10 may only be inserted to a depth within the patient's bone until step 46 contacts or engages enlarged guide pin portion 48. In other words, enlarged inner diameter 42 of enlarged inner diameter portion 38 of interior cannula track 18 may be sized to receive enlarged guide pin portion 48, whereas reduced inner diameter 44 of reduced inner diameter portion 40 may be sized to receive smaller guide pin portion 50, but may be too small to receive enlarged guide pin portion 48. In this manner, as shaft 16 is advanced longitudinally along guide pin 14, reamer device 10 may move freely until step 46 within interior cannula track 18 contacts enlarged guide pin portion 48, at which point shaft 16 is restricted from (and in some cases entirely prevented from) further longitudinal movement along guide pin 14 towards the patient's bone in which guide pin 14 is inserted (e.g., enlarged guide pin portion 48 may be configured to limit the extent to which reamer device 10 may be inserted onto guide pin 14).

Enlarged guide pin portion 48 may be positioned at or near leading end 49 of guide pin 14 (e.g., the end of guide pin 14 that is inserted into the patient's bone). Smaller guide pin portion 50 extends from enlarged guide pin portion 48 to or towards trailing end 51 of guide pin 14, opposite leading end 49. Enlarged guide pin portion 48 is generally sized to extend laterally from the patient's glenoid surface, but ends at a position medial to the patient's humeral head. In other words, guide pin 14 may have an overall guide pin length 53 that extends sufficiently for accurate insertion of guide pin 14 into shaft 16 of reamer device 10, but a length 55 of enlarged guide pin portion 48 may be sized relative to cutter head portion 30 to allow space to engage guide pin 14 between an end of enlarged guide pin portion 48 and the patient's humeral head. In some examples, guide pin 14 (e.g., enlarged guide pin portion 48 of guide pin 14) may include a plurality of markings configured for gauging the extent to which reamer device 10 has been inserted onto guide pin 14, and/or the extent to which guide pin 14 has been inserted into the patient's bone.

Slot 28 may be defined by an opening width 52 and a slot length 54 (e.g., the dimension of slot 28 along longitudinal axis 36). Slot length 54 may be defined as the longitudinal distance between a proximal slot end 56 and a distal slot end 58. As shown in FIG. 1, distal slot end 58 is formed in cutter head portion 30 (e.g., slot 28 extends through cutter head portion 30) and generally corresponds with distal end 22 of shaft 16. In some examples, proximal slot end 56 is positioned between proximal end 20 and distal end 22 of shaft 16. In some examples, slot 28 extends along the entire length of shaft 16 and thus proximal slot end 56 is positioned at proximal end 20 of shaft 16 in these examples. Proximal slot end 56 may capture guide pin 14 within interior cannula track 18 such that once guide pin 14 is received within interior cannula track 18, proximal slot end 56 (and the portion of shaft 16 proximal to proximal slot end 56) is configured to prevent accidental removal of guide pin 14 between proximal slot end 56 and proximal end 20 of shaft 16.

Reamer device 10 is configured such that slot length 54 is sufficient for engagement of interior cannula track 18 with guide pin 14, at a position within the patient's body that is interior to the patient's humeral head. Furthermore, reamer device 10 is generally engaged with guide pin 14 at a location that is between the patient's humeral head and enlarged guide pin portion 48 (e.g., reamer device 10 is initially engaged with smaller guide pin portion 50 and then advanced longitudinally along guide pin 14 to engage enlarged guide pin portion 48). In other words, when guide pin 14 is inserted into a patient's glenoid, slot length 54 and opening width 52 are sufficient such that shaft 16 may be engaged with guide pin 14 at a location interior to (e.g., medial to) the patient's humeral head, rather than being engaged with the guide pin lateral to the patient's humeral head (in which case the device would have to be advanced past the patient's humeral head along the guide pin while already engaged with the guide pin). In this manner, risk of damage to the patient's humeral head and surrounding tissues is minimized as compared to prior art techniques and devices. Furthermore, reamer device 10 may be configured such that cutter head portion 30 is coupled to shaft 16 and in a cutting position (e.g., positioned to cut a patient's bone) when guide pin 14 is received within interior cannula track 18. For example, no subsequent actions may be required to put reamer device 10 in an operative position (e.g., operable to ream a patient's bone) after engagement with guide pin 14 and positioned with respect to the patient's bone.

Opening width 52 may be sized according to guide pin 14. For example, opening width 52 of slot 28 may be smaller than a first diameter 60 of enlarged guide pin portion 48, such that enlarged guide pin portion 48 may not pass through slot 28. On the other hand, opening width 52 of slot 28 may be approximately equal to or larger than a second diameter 62 of smaller guide pin portion 50, such that smaller guide pin portion 50 may pass through slot 28 and into interior cannula track 18. In this manner, once shaft 16 is advanced onto guide pin 14 such that enlarged guide pin portion 48 is within interior cannula track 18 (e.g., within enlarged inner diameter portion 38 of interior cannula track 18), shaft 16 may be configured to capture guide pin 14 within interior cannula track 18 by preventing passage of enlarged guide pin portion 48 through slot 28.

In some examples, shaft 16 may include a coupling structure 63, such as a threaded portion 64, for coupling shaft 16 to a drill (e.g., drill 75 in FIG. 12) or other device. Additionally or alternatively, coupling structure 63 may include other structures, such as interlocking engaging features, ribs, snaps, press-fit features, or any other structures configured for coupling shaft 16 to such devices. For example, coupling structure 63 may be positioned or formed in or on outer surface 26 of shaft 16. In other examples, coupling structure 63 may be positioned or formed in or on inner surface 24 of shaft 16. Coupling structure 63 is generally positioned proximal to slot 28, and may be positioned at or near proximal end 20 of shaft 16. In examples including threaded portion 64, threaded portion 64 may be a reverse threaded portion in some examples. Once reamer device 10 is positioned within a patient's body such that cutter head portion 30 is positioned such that it is configured to cut the patient's bone, cutter head portion 30 may be rotated at a speed sufficient to cut the patient's bone as desired. Coupling structure 63 may be configured to operatively couple shaft 16 to a device configured to cause such rotation of cutter head portion 30 with respect to the patient's bone. For example, coupling structure 63 may be configured to operatively couple reamer device 10 to a drill chuck, a quick-connect guide, a drill, and/or a drive shaft that is configured to cause rotation of cutter head portion 30 about longitudinal axis 36 of shaft 16, generally simultaneously causing rotation of shaft 16 about guide pin 14 received within interior cannula track 18.

Cutter head portion 30 includes a cutting surface 66 that is formed of a material configured to cut the patient's bone. Cutting surface 66 may include, for example, teeth, grooves, blades, and/or graters. Additionally or alternatively, cutter head portion 30 may include one or more relief holes 68 configured to receive and clear away bone fragments generated during use of reamer device 10. Cutter head portion 30 may include one, two, three, four, or more cutting blade lobes 70 (e.g., first cutting blade lobe 70 and second cutting blade lobe 70'). Such cutting blade lobes 70 may be oriented such that they are spaced apart substantially equidistantly from one another about longitudinal axis 36 of shaft 16, though other arrangements are also possible. The size and/or shape of cutting blade lobes 70 may be optimized or designed to reduce potential trauma to the patient's humeral head, or other anatomy. For example, cutting blade lobes 70 may be designed to be smaller and/or thinner than conventional cutting blades, so as to minimize the risk of damage to the patient during use of reamer device 10. Cutter head portion 30 is generally formed integrally with and/or permanently secured to shaft 16 (e.g., cutter head portion 30 may not be removable or detachable from shaft 16 without damage or destruction to shaft 16), though, in some examples, cutter head portion and/or one or more cutting blade lobes 70 may be selectively removable and re-attachable from/to shaft 16.

In some examples, reamer device 10 may include an annular stop 72 positioned on outer surface 26 of shaft 16. Annular stop 72 may be configured to act in conjunction with a shaft handle mechanism or sleeve (such as shaft handle 71 shown in FIG. 12) that a user may use to guide, apply forward pressure to, and/or direct reamer device 10 while in use. Annular stop 72 may be positioned proximal to slot 28 (e.g., proximal to proximal slot end 56). Annular stop 72 may include a centering relief 73 that is configured to guide guide pin 14 into interior cannula track 18 of reamer device 10. Additionally or alternatively, reamer device 10 may include a finger relief 74 configured to allow pressure to be applied to guide pin 14 located radially inward from outer surface 26 of shaft 16 (e.g., within interior cannula track 18). In other words, finger relief 74 may represent a portion of shaft 16 that is recessed with respect to the remainder of shaft 16 in order to provide access to guide pin 14 positioned within interior cannula track 18, such that a user may push and/or help retain guide pin 14 in interior cannula track 18.

In some examples, reamer device 10 includes a sliding ring 76 that is configured to engage outer surface 26 of shaft 16, and slide longitudinally with respect to shaft 16 and slot 28 (e.g., along longitudinal axis 36). Sliding ring 76 may be configured to capture guide pin 14 within interior cannula track 18 in examples of reamer device 10 where slot 28 extends along the entire length of shaft 16 to proximal end 20, as indicated by dashed line 78 in FIG. 1. In these examples, sliding ring 76 may be selectively positioned on shaft 16 once reamer device 10 is engaged with guide pin 14, such that sliding ring 76 prevents premature removal of guide pin 14 from within interior cannula track 18. Some systems 12 additionally may include a guide handle tool 80 (which may also be referred to as a ring tool 80) that is configured to move sliding ring 76 relative to shaft 16 and slot 28, thereby positioning sliding ring 76 as desired. In some examples, guide handle tool 80 is configured to secure sliding ring 76 in a selected position relative to shaft 16 and slot 28. Additionally or alternatively, sliding ring 76 may be secured in a selected position by another mechanism, such as with a friction engagement with shaft 16 and/or a pin/spring detent mechanism.

Some reamer devices 10 may include a plurality of slots 28. For example, reamer device 10 may include two slots, such as a medial slot 82 and a lateral slot 84, both of which may be examples of slots 28. In some such examples, medial slot 82 and lateral slot 84 may be positioned adjacent one another, or separated from one another. In some examples, medial slot 82 and lateral slot 84 may be positioned on opposite sides of shaft 16 from one another. In some examples, one of medial slot 82 and lateral slot 84 may be positioned adjacent cutter head portion 30, while the other of medial slot 82 and lateral slot 84 may be positioned proximally (e.g., closer to proximal end 20). Medial slot 82 and lateral slot 84 may be configured to facilitate alignment of shaft 16 with guide pin 14. Additionally or alternatively, medial slot 82 and lateral slot 84 may be configured to allow pivoting of shaft 16 anteriorly in an axial plane of the patient's body prior to final engagement of cutter head portion 30 with guide pin 14.

As opposed to being designed for patient specific instrumentation, some reamer devices 10 may be configured to be used on a plurality of different patients. To this end, reamer device 10 may be configured to be sterilized and reused. In other examples, reamer device 10 may be configured for use as a patient-specific device.

Additionally or alternatively, reamer device 10 may include one or more anti-rotation features 86 configured to prevent rotation of cutter head portion 30 with respect to shaft 16. Examples of such anti-rotation features 86 may include threads, splines, and/or a non-circular cross-sectional area of shaft 16, interior cannula track 18, and/or guide pin 14.

Turning now to FIGS. 2-16, examples of components of systems 12 in the form of reamer devices 10, guide pins 14, and guide handle tools 80 are illustrated. Where appropriate, the reference numerals from the schematic illustrations of FIG. 1 are used to designate corresponding parts of reamer devices 10 and guide pins 14; however, the examples of FIGS. 2-16 are non-exclusive and do not limit reamer devices 10, guide pins 14, and guide handle tools 80 to the illustrated embodiments. That is, reamer device 10 and guide pin 14 are not limited to the specific embodiments illustrated in FIGS. 2-16, and may incorporate any number of the various aspects, configurations, characteristics, properties, etc. that are illustrated in and discussed with reference to the schematic representation of FIG. 1 and/or the embodiments of FIGS. 2-16, as well as variations thereof, without requiring the inclusion of all such aspects, configurations, characteristics, properties, etc. In addition, system 12 of FIG. 1 may include the reamer device 10, guide pin 14, and/or guide handle tool 80, and/or components thereof, of any of FIGS. 2-16 without departing from the scope of the present disclosure. This is indicated schematically in FIGS. 2-16 by the inclusion of reference numerals 10, 14, and 80. For the purpose of brevity, each previously discussed component, part, portion, aspect, region, etc. or variants thereof may not be discussed, illustrated, and/or labeled again; however, it is within the scope of the present disclosure that the previously discussed features, variants, etc. may be utilized with presently disclosed reamer devices, guide pins, and guide handle tools.

FIGS. 2-3 illustrate reamer device 88, which is an example of reamer device 10. In this example, cutter head portion 30 includes two cutting blade lobes 70 that are positioned approximately 180 degrees from one another, about shaft 16. Cutting blade lobes 70 are shaped to include a substantially flat edge 90 and a curved edge 92, though other shapes are within the scope of the present disclosure. Cutter head portion 30 is generally propeller-shaped, though other shapes are possible. Shaft 16 extends proximally from cutter head portion 30, and interior cannula track 18 is formed through the center of shaft 16 and cutter head portion 30. Within interior cannula track 18 is enlarged inner diameter portion 38, to accommodate enlarged guide pin portion 48 of guide pin 14 of FIG. 4. Reduced inner diameter portion 40 of interior cannula track 18 is sized to receive smaller guide pin portion 50 of guide pin 14 of FIG. 4. Smaller guide pin portion 50 is sized to pass through slot 28 formed in shaft 16, so that guide pin 14 may be positioned within interior cannula track 18, as explained in connection with FIGS. 5-6. Guide pin 14 of FIG. 4 includes markings 94 near leading end 49 (e.g., on enlarged guide pin portion 48) to indicate the depth to which guide pin 14 has been inserted into a patient's bone, but in other examples, guide pin 14 need not include such markings 94.

Figure 6:
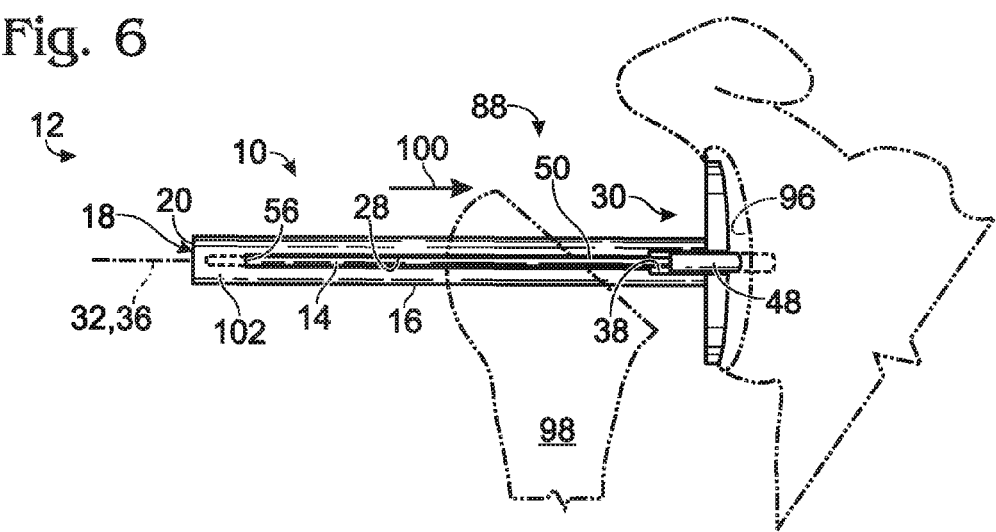
FIG. 6 is a side elevation view of the reamer device of FIG. 5, positioned on the guide pin inserted in the patient's bone.

FIGS. 5-6 show reamer device 88 of FIGS. 2-3 being inserted onto guide pin 14, which is shown inserted into a schematically-represented glenoid 96 (FIG. 6). As shown in FIG. 6, enlarged guide pin portion 48 of guide pin 14 is partially inserted into glenoid 96, with smaller guide pin portion 50 extending from enlarged guide pin portion 48. To engage reamer device 10 with guide pin 14, as shown in FIG. 5, reamer device 88 is aligned with respect to guide pin 14 such that slot 28 faces guide pin 14, and then cutter head portion 30 is moved towards guide pin 14. As shown in FIG. 5, reamer device 88 may be arranged such that longitudinal axis 36 of shaft 16 is at a non-parallel angle with respect to longitudinal axis 32 of guide pin 14. Reamer device 10 may be moved (e.g., laterally and/or posteriorly) with respect to guide pin 14 until slot 28 engages guide pin 14 adjacent cutter head portion 30. Smaller guide pin portion 50 may be engaged when cutter head portion 30 is at a position between enlarged guide pin portion 48 and a humeral head 98 of the patient.

FIG. 5 illustrates reamer device 88 from above, looking down on the patient's shoulder, which illustrates that the reamer device may be moved posteriorly (e.g., towards the patient's back) as it is engaged with guide pin 14, in some examples. Shaft 16 is then pivoted with respect to guide pin 14 until guide pin 14 is received within interior cannula track 18 of reamer device 88, as shown in FIG. 6. As shaft 16 is pivoted, smaller guide pin portion 50 enters shaft 16 by passing through slot 28 until it is received within interior cannula track 18. Once longitudinal axis 36 of shaft 16 is substantially parallel to longitudinal axis 32 of guide pin 14, reamer device 88 is said to be fully engaged with guide pin 14. FIG. 6 illustrates reamer device 88 from an elevation view, looking into the patient's body from the front/anterior side; reamer device 88 has been rotated about guide pin 14 for clarity, and to show guide pin 14 with respect to slot 28.

Once reamer device 88 has been fully engaged with guide pin 14, reamer device 88 is advanced longitudinally along guide pin 14, in a medial direction towards glenoid 96 (in the direction indicated by arrow 100 in FIG. 6). In other words, reamer device 88 is moved longitudinally with respect to guide pin 14, once guide pin 14 is received within interior cannula track 18 of reamer device 88. As shown in FIG. 6, once reamer device 88 is advanced along guide pin 14 towards glenoid 96, guide pin 14 may be captured within shaft 16, such as by a proximal portion 102 of shaft 16, which extends from proximal slot end 56 to proximal end 20 of shaft 16. Additionally, enlarged guide pin portion 48 may have a diameter that is too large to pass through slot 28, thereby preventing removal of guide pin 14 through slot 28 adjacent cutter head portion 30 once reamer device 88 is advanced onto enlarged guide pin portion 48 (so that enlarged guide pin portion 48 is positioned within enlarged inner diameter portion 38 of interior cannula track 18). Once reamer device is adequately advanced along guide pin 14 towards glenoid 96, cutter head portion 30 is now configured and positioned such that rotation of cutter head portion 30 about guide pin 14 reams glenoid 96 during a shoulder arthroplasty procedure.

Figure 7:
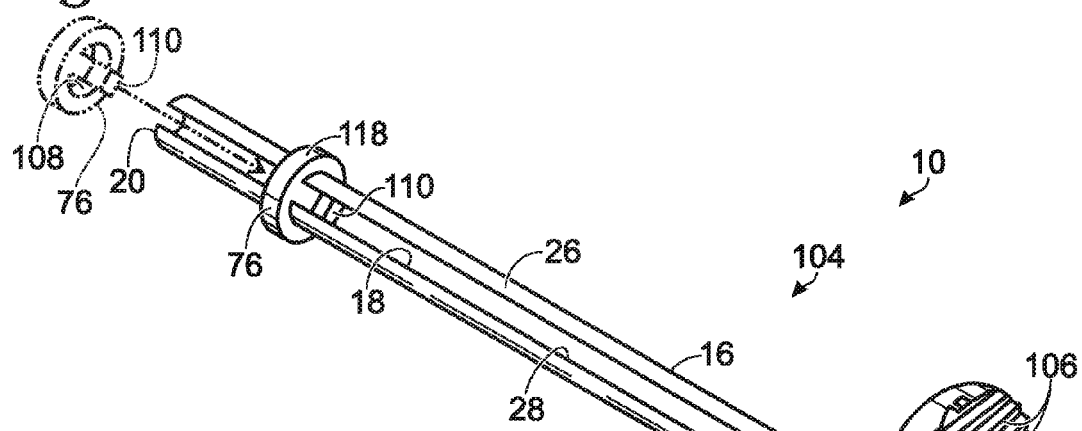
FIG. 7 is a perspective view of another example of a reamer device having a sliding ring, according to the present disclosure.

FIG. 7 illustrates another example of reamer device 10, in the form of reamer device 104. Slot 28 of reamer device 104 extends from distal end 22 to proximal end 20 of shaft 16, thereby exposing interior cannula track 18 along the entire length of reamer device 104. Cutting blade lobes 70 are shaped similarly to those of reamer device 88 of FIGS. 2-3, but additionally include cutting blades and teeth 106 formed on lobes 70. Sliding ring 76 is used to capture a guide pin (e.g., guide pin 14) within interior cannula track 18 of reamer device 104. As with other examples, reamer device 104 is moved laterally and/or posteriorly with respect to a guide pin such that the guide pin passes through slot 28 until it is received within interior cannula track 18. Reamer device 104 can then be moved along the guide pin (e.g., longitudinally with respect to the guide pin) while the guide pin is positioned in interior cannula track 18.

Once reamer device 104 is engaged with a guide pin, sliding ring 76 may be positioned on shaft 16 to retain the guide pin within interior cannula track 18. For example, sliding ring 76 includes an inner surface 108 that may be engaged with outer surface 26 of shaft 16. A protrusion 110 may extend radially inward from inner surface 108 of sliding ring 76, and protrusion 110 may be sized and shaped to be positioned within slot 28 of shaft 16. Protrusion 110 may be configured to prevent rotation of sliding ring 76 about longitudinal axis 36 of shaft 16, while protrusion 110 is engaged with slot 28 (e.g., while protrusion 110 is positioned to extend at least partially through slot 28), though sliding ring 76 may be selectively moved longitudinally with respect to shaft 16, along longitudinal axis 36 (FIG. 7 illustrates sliding ring 76 in dashed line, positioned adjacent shaft 16, and in solid line, after being selectively moved longitudinally with respect to shaft 16). In some examples, sliding ring 76 may be selectively secured in place, such that once it is positioned to capture a guide pin within reamer device 104, it may be selectively and reversibly prevented from moving longitudinally along shaft 16 while reamer device 104 is in use.

Figure 8:
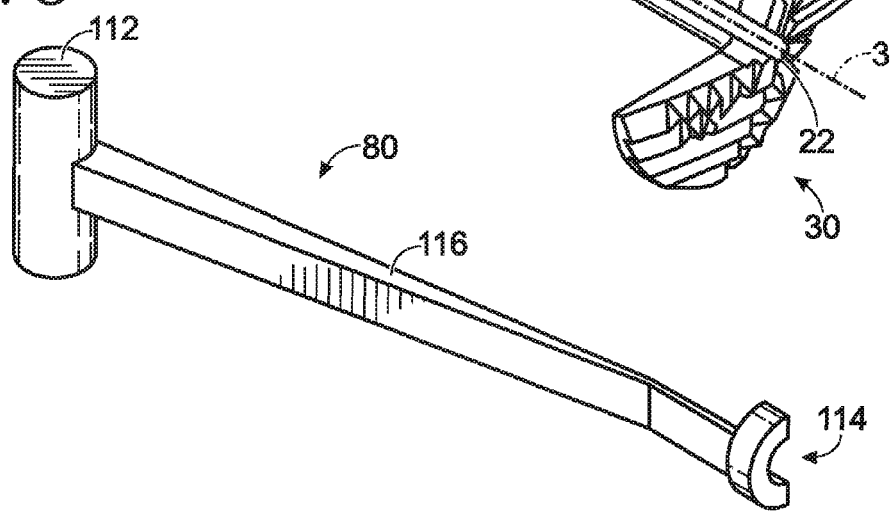
FIG. 8 is a perspective view of a guide handle tool for use with presently disclosed reamer devices.

FIG. 8 shows one example of guide handle tool 80 that may be used to position sliding ring 76 onto shaft 76, though in some examples, sliding ring 76 may be positioned by hand, without such a guide handle tool 80. Guide handle tool 80 generally includes a handle 112 for engagement by a user, and a guide portion 114 separated from handle 112 by a tool shaft 116. Guide portion 114 may be shaped and sized to engage sliding ring 76, such as having complementary curvature to engage an outer surface 118 of sliding ring 76. Guide portion 114 may grasp or interconnect with sliding ring 76 upon manipulation of handle 112 in some examples.

In other examples, guide handle tool 80 may be simply designed to move sliding ring 76 along shaft 16.

FIGS. 9 and 10 show alternate examples of cutter head portions 30 that may be used with reamer devices 10 according to the present disclosure. In FIG. 9, cutting blade lobes 70 are thinner than other illustrated examples, which may facilitate a further reduction in potential damage to the patient's tissues while engaging the reamer device with a guide pin within the patient's body. The example of cutter head portion 30 shown in FIG. 10, on the other hand includes just a single cutting blade lobe 70. These are not meant to be limiting, and other cutter head portion designs are also possible. The cutter head portions illustrated in FIGS. 9-10 may be used with any of the reamer devices 10 disclosed herein.

FIG. 11 illustrates reamer device 120, which is an example of reamer device 10. Reamer device 120 includes shaft 16 with interior cannula track 18 extending therethrough. Reamer device 120 is not shown with a slot (e.g., slot 28) formed through shaft 16, though it may include such a slot in some examples, and/or may include slot 28 formed at least through cutter head portion 30. Contrary to other illustrated examples, reamer device 120 includes a cutter head portion 121 (which is an example of cutter head portion 30) that may be selectively detached from and attached to shaft 16. In this example, cutter head portion 121 is shown detached from shaft 16, and shaft 16 includes a hex end 122 at proximal end 22 of shaft 16. Hex end 122 is configured to engage with cutter head portion 121, such as by engaging a receiving portion 124 of cutter head portion 121. While FIG. 11 illustrates a hex end 122, in other examples other mechanisms for detaching and removing cutter head portion 121 from shaft 16 may be used. For example, threads, snaps, slots, ratchets, and/or any other suitable mechanism may be used to secure a removable cutter head portion as shown in FIG. 11. In these examples, cutter head portion 121 may be secured to shaft 16 at a location inside the patient's body, between the patient's humeral head and glenoid surface. For example, reamer device 120 may be inserted into a patient's body while disassembled (e.g., with cutter head portion 121 separated from shaft 16), and cutter head portion 121 may be secured to shaft 16 before use. In this manner, cutter head portion 121 and shaft 16 may be advanced past the patient's humeral head without as much restriction on relative movement of the components as if they were assembled.

FIG. 12 illustrates another example of reamer device 10, in the form of reamer device 126. Reamer device 126 is similar to other examples of reamer device 10, having a cutter head portion 30 with a slot 28 formed through it and extending longitudinally along shaft 16. Reamer device 126 also includes an annular stop 72 positioned near proximal end 20 of shaft 16. Annular stop 72 may be positioned proximal to proximal slot end 56, as shown, but in other examples may be positioned closer to or even overlapping with slot 28, and/or may be positioned close to or at proximal end 20 of shaft 16. Annular stop 72 may be configured to act in conjunction with shaft handle 71 (which also may be referred to as sleeve 71) that a user may use to guide, apply forward pressure to, and/or direct reamer device 126 while in use. In some examples, a centering relief 73 on the proximal side of annular stop 72 may be curved to receive a portion of a user's finger or fingers during use of reamer device 126 so that the user can more easily manipulate the positioning and orientation of reamer device 126 and guide it onto a guide pin. Additionally or alternatively, annular stop 72 may be configured to act as a stop for a secondary device. For example, a user may employ the use of a separate handle device to help guide and position reamer device 126, and annular stop 72 may serve to prevent movement of the separate handle device distal to annular stop 72 (e.g., the separate handle device and/or shaft handle 71 may push against annular stop 72 as a user advances it distally along shaft 16).

FIG. 12 also illustrates drill 75, which is operatively coupled to reamer device 126 such that drill 75 causes rotation of cutter head portion 30 about the longitudinal axis of shaft 16 (and rotation of shaft 16 about a guide pin positioned therein, such as guide pin 14). For example, drill 75 may be coupled to a coupling structure (e.g., coupling structure 63) near proximal end 20 of shaft 16, as shown. A drive shaft 77 of drill 75 extends through shaft handle 71 in this example.

FIGS. 13-14 illustrate yet another example of reamer device 10, in the form of reamer device 128. Reamer device 128 includes a finger relief 74, which is shown in profile in FIG. 13, and in an isometric view in FIG. 14. Finger relief 74 allows a user to press a guide pin into interior cannula track 18 by positioning his or her finger within finger relief 74, and pressing radially inward. Because finger relief 74 is a recess formed into shaft 16, it allows a user to press farther radially inward than simply pressing a guide pin through slot 28 (e.g., because a user can only press as far as outer surface 26 of shaft 16 allows, and thus a user may not be able to press a guide pin all the way through slot 28 from the outside of shaft 16). In other words, finger relief 74 may be configured to provide direct access to interior cannula track 18. Additionally, finger relief 74 is positioned proximal to slot 28, and/or adjacent proximal slot end 56, which may be easier for a user to access during use, when distal end 22 of reamer device 128 is positioned within a patient's body. Reamer device 128 may also include a centering channel 130 formed in finger relief 74, which may be a conical flare formed in the proximal portion of reamer device 128 (e.g., near proximal end 20, and/or at least proximal to slot 28), which may be configured to help guide a guide pin into interior cannula track 18 as reamer device 128 is being engaged with the guide pin.

FIGS. 15-16 illustrate reamer device 132, which is another example of reamer device 10. Reamer device 132 is shown from the left in FIG. 15, and from the right in FIG. 16, to illustrate the inclusion of two slots formed in shaft 16. Instead of including a single slot 28, the device may include a first slot 134 and a second slot 136, each of first slot 134 and second slot 136 being configured to allow a guide pin to pass there though and into interior cannula track 18 of shaft 16. In some examples, first slot 134 is a medial slot (e.g., medial slot 82) and second slot 136 is a lateral slot (e.g., lateral slot 84), such that first slot 134 and second slot 136 are positioned on opposite sides of shaft 16. Additionally, first slot 134 is positioned distal to second slot 136 in reamer device 132 (e.g., second slot 136 is positioned nearer to proximal end 20 than is first slot 134, while first slot 134 is positioned at cutter head portion 30 and extends towards proximal end 20 from cutter head portion 30). In other examples, the arrangement may be switched, such that first slot 134 may be positioned proximal to second slot 136, such that second slot 136 may be positioned at cutter head portion 30 and extend towards proximal end 20, while first slot 134 may be positioned nearer to proximal end 20.

Such an arrangement as shown in FIGS. 15-16 may be configured to facilitate alignment of reamer device 132 with a guide pin (e.g., guide pin 14) in some examples. Additionally or alternatively, reamer device 132 may be configured to allow pivoting of shaft 16 anteriorly in an axial plane of the patient's body prior to final engagement of cutter head portion 30 with a guide pin. For example, reamer device 132 may be initially engaged with a guide pin via second slot 136, and then later engaged with a guide pin via first slot 134.

Figure 17:
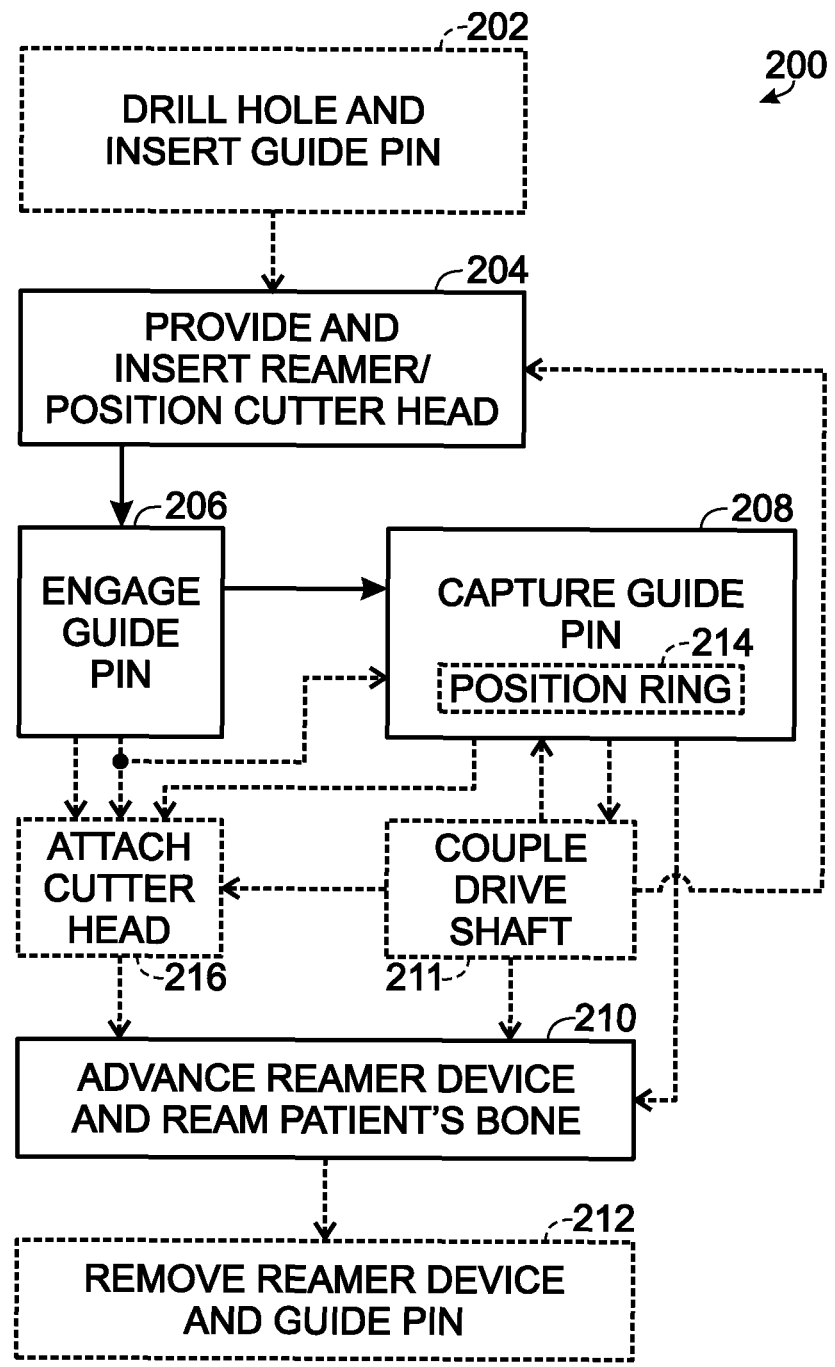
FIG. 17 is a schematic flowchart diagram illustrating methods according to the present disclosure.

FIG. 17 schematically provides a flowchart that represents illustrative, non-exclusive examples of methods 200 according to the present disclosure. In FIG. 17, some steps are illustrated in dashed boxes indicating that such steps may be optional or may correspond to an optional version of a method 200 according to the present disclosure. That said, not all methods according to the present disclosure are required to include the steps illustrated in solid boxes. The methods and steps illustrated in FIG. 17 are not limiting and other methods and steps are within the scope of the present disclosure, including methods having greater than or fewer than the number of steps illustrated, as understood from the discussions herein.

Methods 200 of using presently disclosed reamer devices (e.g., reamer device 10) to prepare a patient's bone for receiving an implant component (e.g., reaming the surface of a patient's glenoid during a shoulder arthroplasty) generally include inserting a guide pin (e.g., guide pin 14) into a patient's glenoid at 202, providing and positioning a reamer device according to the present disclosure at 204, engaging the reamer device with or onto the guide pin at 206, and capturing the guide pin within the shaft (e.g., within interior cannula track 18 of shaft 16 of reamer device 10) at 208. As the reamer device is positioned at 204, the cutter head portion of the reamer device is generally placed in proximity to the guide pin such that the shaft of the reamer device is oriented at a non-parallel angle with respect to the guide pin (e.g., as shown in FIG. 5), with a slot of the reamer device (e.g., slot 28) aligned such that it is facing the guide pin.

Generally, inserting the guide pin at 202 includes simultaneously drilling a hole using the guide pin, such as by using a drill tip (e.g., cutting point 47) at a leading end (e.g., leading end 49) of the guide pin. In some examples where the guide pin is a dual diameter guide pin (e.g., having enlarged guide pin portion 48 and smaller guide pin portion 50), the guide pin may be inserted into the patient's glenoid at 202 to a depth such that a portion of the enlarged guide pin portion extends from the patient's bone, rather than inserting the guide pin such that the enlarged guide pin portion (if present) is entirely inserted into the patient's bone. In this manner, the guide pin may engage features within the reamer device (e.g., step 46 between enlarged inner diameter portion 38 and reduced inner diameter portion 40 of interior cannula track 18 within shaft 16) to limit the depth to which the reamer device is advanced along the guide pin and inserted into the patient's body. For example, the reamer device may be inserted eccentrically into the patient's shoulder cavity, and engaging the reamer device with the guide pin at 206 may include moving the reamer device laterally and/or posteriorly with respect to the guide pin such that the shaft is positioned onto the smaller guide pin portion, with the enlarged guide pin portion being positioned distal (e.g., medial) to the smaller guide pin portion and initial point of engagement between the guide pin and the reamer device. The reamer device may then be advanced longitudinally with respect to the guide pin until the step formed within the interior cannula track engages the enlarged guide pin portion (at which point the enlarged guide pin portion of the guide pin will be positioned in the enlarged inner diameter portion of the interior cannula track, and the smaller guide pin portion of the guide pin will be positioned in the reduced inner diameter portion of the interior cannula track).

This relationship between the guide pin and reamer device can be configured to ensure or facilitate proper positioning of the cutter head portion (e.g., cutter head portion 30) of the reamer device with respect to the patient's bone. In this manner, once engaged together, the reamer device may be advanced along the guide pin until the enlarged guide pin portion is received within the enlarged inner diameter portion of the interior cannula track and until the step abuts or contacts the enlarged guide pin portion, thereby stopping further advancement of the reamer device in a longitudinal direction along the guide pin.

Engaging the reamer device with the guide pin at 206 (e.g., positioning the guide pin within the interior cannula track 18 of the shaft of the reamer device) may be performed at a location in the patient's body between the patient's humeral head and the patient's glenoid (e.g., medial to the humeral head and lateral to the glenoid), such that the cutter head portion of the reamer device poses less of a risk of damage to the patient's humeral head and surrounding tissues. In prior art techniques, the reamer device would be engaged with the guide pin before it is advanced past the patient's humeral head towards the glenoid, increasing the risk of damage to the humeral head by virtue of close proximity of the guide pin to the humeral head. By contrast, with the presently disclosed reamer devices, the reamer device may be engaged with the guide pin "later," such that the guide pin is not positioned within the shaft as the cutter head portion is moved past the humeral head. For example, presently disclosed reamer devices may be aligned with respect to the guide pin such that the slot formed in the shaft of the reamer device faces the guide pin, and then moved laterally and/or posteriorly towards the guide pin until the guide pin passes radially through the slot and is received within the interior cannula track of the reamer device. In some methods, engaging the guide pin at 206 includes moving the cutter head portion towards the guide pin until the portion of the slot formed in the cutter head is moved onto the guide pin, and then pivoting the shaft towards the guide pin until the longitudinal axes of the guide pin and the shaft are substantially parallel and the guide pin is received within the interior cannula track after passing through the remaining portion of the slot. Engagement of the guide pin through the slot formed in the shaft allows the guide pin to be placed within the interior cannula track of the reamer device by radial movement of the shaft with respect to the guide pin, rather than solely longitudinal movement. Engagement of the guide pin in this manner by presently disclosed reamer devices can advantageously substantially avoid bending the guide pin while engaging and capturing the guide pin, which can increase accuracy and reduce the likelihood of guide pin fractures or other damage.

Once the reamer device is fully engaged with the guide pin, the reamer device may be advanced longitudinally along the guide pin and the patient's bone may be cut, or reamed, at 210. For example, the reamer device may be slid with respect to the guide pin until the cutter head portion is positioned appropriately with respect to the patient's bone surface (e.g., glenoid). The reamer device may be operatively coupled to a drill (e.g., drill 75) or other device before or after engagement with the guide pin, to cause rotation of the cutter head portion about the guide pin, in order to cut the patient's bone (e.g., remove a portion of the glenoid surface in preparation for receiving an implant component). For example, a drill chuck and/or drive shaft connected to a drill or other suitable device may be coupled to the proximal end of the shaft at 211. After reaming is complete, the reamer device and guide pin may be removed from the patient at 212. In some methods 200, removing the reamer device at 212 includes disengaging the drill from the reamer device, and disengaging the reamer device from the guide pin (e.g., by moving the reamer device laterally away from the guide pin such that the guide pin passes through the slot and exits the interior cannula track of the reamer device) before moving the cutter head portion lateral to the patient's humeral head and completely removing the reamer device from the patient's body.

Capturing the guide pin within the interior cannula track at 208 is configured to prevent the guide pin from being prematurely removed from the slot of the reamer device. For example, the guide pin may be captured within the shaft/interior cannula track at 208 by pivoting the shaft with respect to the guide pin such that the guide pin is received within the interior cannula track and a proximal portion of the shaft (e.g., proximal portion 102 of shaft 16) proximal to the proximal end of the slot (e.g., proximal slot end 56) prevents the proximal end of the guide pin from radially exiting the interior cannula track through the slot, thereby capturing the guide pin within the interior cannula track. In some methods, capturing the guide pin at 208 may include positioning a sliding ring (e.g., sliding ring 76) onto the shaft at 214 such that it engages the slot and the outer surface of the shaft, and such that it prevents premature removal of the guide pin from the slot of the reamer device.

Some methods 200 include coupling a selectively detachable cutter head portion (e.g., removable cutter head portion 121) to the shaft within the patient's shoulder cavity at 216. In some methods, inserting the guide pin at 202 includes inserting the guide pin to a predetermined depth within the patient's glenoid. Accordingly, drilling the hole and inserting the guide pin at 202 may include drilling a hole of a predetermined depth configured to receive the desired length of the guide pin. While methods 200 are generally referred to as relating to a particular form of shoulder surgery, it is to be understood that systems and devices disclosed herein may be applicable to other methods and other surgical techniques apart from those specifically described herein.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entity in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" may mean A alone, B alone, C alone, A and B together, A and C together, B and C together, A, B and C together, and optionally any of the above in combination with at least one other entity.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the terms "selective" and "selectively," when modifying an action, movement, configuration, or other activity of one or more components or characteristics of an apparatus, mean that the specific action, movement, configuration, or other activity is a direct or indirect result of user manipulation of an aspect of, or one or more components of, the apparatus.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

Examples of shoulder reamer devices and related systems and methods according to the present disclosure are described in the following enumerated paragraphs:

A1. A reamer device, comprising:
 a shaft extending from a proximal end to a distal end, the shaft comprising:
  an inner surface defining an interior cannula track, wherein the shaft is configured to receive a guide pin within the interior cannula track such that the guide pin is substantially parallel with the interior cannula track when received in the interior cannula track;
  an outer surface opposite the inner surface; and
  a slot formed in the outer surface of the shaft, wherein the slot extends longitudinally along the shaft from the distal end of the shaft towards the proximal end of the shaft, and wherein the slot extends radially from the outer surface of the shaft to the interior cannula track; and
 a cutter head portion positioned at the distal end of the shaft, the cutter head portion being configured to cut a patient's bone, wherein the interior cannula track and the slot extend through the cutter head portion.

A1.1. The reamer device of paragraph A1, wherein the reamer device is configured to receive a guide pin within the interior cannula track by passing the guide pin through the slot.

A2. The reamer device of paragraph A1 or A.1.1, wherein the reamer device is configured to prepare a patient's glenoid for shoulder arthroplasty.

A3. The reamer device of any of paragraphs A1-A2, wherein the reamer device is configured to cut a patient's glenoid surface in the course of shoulder arthroplasty.

A4. The reamer device of any of paragraphs A1-A3, wherein the shaft is configured to slide longitudinally with respect to a/the guide pin positioned within the interior cannula track.

A5. The reamer device of any of paragraphs A1-A4, wherein the shaft is configured such that it may be placed onto a/the guide pin by lateral and/or posterior movement of the shaft with respect to the guide pin.

A6. The reamer device of any of paragraphs A1-A5, wherein the shaft is configured such that movement of the shaft in a direction that is orthogonal to a longitudinal axis of a/the guide pin, such that the guide pin passes through the slot, causes the guide pin to be received in the interior cannula track.

A7. The reamer device of any of paragraphs A1-A6, wherein the shaft is configured to engage a/the guide pin by moving the shaft relative to the guide pin such that a portion of the slot formed in the cutter head portion is placed onto the guide pin.

A8. The reamer device of any of paragraphs A1-A7, wherein the shaft is configured to engage a/the guide pin by pivoting the shaft with respect to the guide pin such that the cutter head portion moves towards the guide pin.

A9. The reamer device of any of paragraphs A1-A8, wherein the shaft is configured to engage a/the guide pin by placing the cutter head portion in proximity to the guide pin such that the shaft is positioned at a non-parallel angle with respect to the guide pin, aligning the slot with the guide pin, moving the cutter head portion towards the guide pin such that a/the portion of the slot formed in the cutter head portion is placed onto the guide pin, and pivoting the shaft towards the guide pin until the guide pin and the shaft are substantially parallel and the guide pin passes through the slot and is received within the interior cannula track.

A10. The reamer device of any of paragraphs A1-A9, wherein the interior cannula track comprises an enlarged inner diameter portion and a reduced inner diameter portion, wherein the enlarged inner diameter portion has an enlarged inner diameter that is greater than a reduced inner diameter of the reduced inner diameter portion of the interior cannula track.

A11. The reamer device of paragraph A10, wherein the enlarged inner diameter portion is adjacent the cutter head portion.

A12. The reamer device of any of paragraphs A10-A11, wherein the enlarged inner diameter portion extends longitudinally from the distal end of the shaft towards the proximal end of the shaft.

A13. The reamer device of any of paragraphs A10-A12, wherein a portion of the interior cannula track positioned through the cutter head portion forms at least a portion of the enlarged inner diameter portion.

A14. The reamer device of any of paragraphs A10-A13, wherein the enlarged inner diameter portion and the reduced inner diameter portion are immediately adjacent one another such that the interior cannula track is a single, continuous track.

A15. The reamer device of any of paragraphs A10-A14, wherein the enlarged inner diameter portion and the reduced inner diameter portion are coaxial.

A16. The reamer device of any of paragraphs A10-A15, wherein the interior cannula track comprises a step formed at an interface of the enlarged inner diameter portion and the reduced inner diameter portion.

A17. The reamer device of paragraph A16, wherein the step is configured to engage a portion of a/the guide pin.

A18. The reamer device of any of paragraphs A16-A17, wherein the step is configured to prevent further longitudinal movement of the shaft relative to a/the guide pin when an enlarged guide pin portion contacts the step.

A19. The reamer device of any of paragraphs A1-A18, wherein the shaft comprises a threaded portion.

A20. The reamer device of paragraph A19, wherein the threaded portion is positioned on the outer surface of the shaft.

A21. The reamer device of any of paragraphs A19-A20, wherein the threaded portion is positioned near the proximal end of the shaft.

A22. The reamer device of any of paragraphs A19-A21, wherein the threaded portion comprises reverse threads.

A23. The reamer device of any of paragraphs A19-A22, wherein the threaded portion is configured to operatively couple the shaft to a drill chuck, a quick-connect guide, and/or a drive shaft configured to couple the reamer device to a drill and cause rotation of the cutter head portion to cut a patient's bone.

A24. The reamer device of any of paragraphs A1-A23, wherein the shaft comprises an annular stop positioned on the outer surface of the shaft, wherein the annular stop is configured to act as a mechanism for a user to guide, apply forward pressure to, and/or direct the reamer device while in use.

A24.1. The reamer device of paragraph A24, wherein the annular stop comprises a centering relief that is configured to guide a/the guide pin into the interior cannula track.

A25. The reamer device of paragraph A24 or A24.1, wherein the annular stop is positioned proximal to the slot formed in the outer surface of the shaft.

A26. The reamer device of any of paragraphs A1-A25, wherein the shaft further comprises a finger relief configured to allow pressure to be applied to a/the guide pin at a location radially inward from the outer surface of the shaft.

A26.1. The reamer device according to paragraph A26, wherein the finger relief is configured to allow a/the user to push the guide pin into the interior cannula track.

A27. The reamer device of any of paragraphs A1-A26.1, wherein the slot has a slot length equal to a longitudinal distance between a proximal slot end and a distal slot end, wherein the distal slot end is formed in the cutter head portion.

A28. The reamer device of paragraph A27, wherein the slot length is sufficient for engagement of the interior cannula track with a/the guide pin at a position within a patient's body that is interior to the patient's humeral head.

A29. The reamer device of paragraph A27 or A28, wherein the distal slot end is positioned at the distal end of the shaft.

A30. The reamer device of any of paragraphs A27-A29, wherein the proximal slot end is positioned between the distal end of the shaft and the proximal end of the shaft.

A30.1. The reamer device of any of paragraphs A27-A29, wherein the proximal slot end is positioned at the proximal end of the shaft.

A31. The reamer device of any of paragraphs A27-A30.1, wherein the proximal slot end is configured to capture a/the guide pin within the interior cannula track, such that once the guide pin is received within the interior cannula track, the proximal slot end prevents the guide pin from accidental removal of the guide pin between the proximal slot end and the proximal end of the shaft.

A32. The reamer device of any of paragraphs A1-A31, wherein the slot has an opening width that is smaller than an enlarged guide pin portion of a/the guide pin on which the interior cannula track is configured to be positioned.

A33. The reamer device of any of paragraphs A1-A32, wherein the slot comprises a medial slot and a lateral slot opposite the medial slot, wherein one of the medial slot and the lateral slot is positioned adjacent the cutter head portion, and wherein the other of the medial slot and the lateral slot is positioned closer to the proximal end of the shaft.

A33.1. The reamer device of paragraph A33, wherein the medial slot and the lateral slot are separated from one another.

A34. The reamer device of paragraph A33 or A33.1, wherein the medial slot and the lateral slot in combination are configured to facilitate alignment of the shaft with a/the guide pin the interior cannula track is configured to receive.

A35. The reamer device of paragraph A33 or A34, wherein the medial slot and the lateral slot in combination are configured to allow pivoting of the shaft anteriorly in an axial plane of the patient's body prior to final engagement of the cutter head portion with the guide pin.

A36. The reamer device of any of paragraphs A1-A35, wherein the cutter head portion comprises a cutting surface having teeth, grooves, blades, and/or graters.

A37. The reamer device of any of paragraphs A1-A36, wherein the reamer device comprises one or more relief holes configured to receive and clear away bone fragments during use of the reamer device.

A38. The reamer device of any of paragraphs A1-A37, wherein the cutter head portion comprises a single lobe cutting blade.

A39. The reamer device of any of paragraphs A1-A38, wherein the cutter head portion comprises a plurality of cutting blade lobes.

A40. The reamer device of any of paragraphs A1-A39, wherein the cutter head portion is sized and/or shaped to reduce potential trauma to the patient's humeral head.

A41. The reamer device of any of paragraphs A1-A40, wherein the cutter head portion is selectively detachable from the shaft.

A42. The reamer device of any of paragraphs A1-A41, wherein the cutter head portion is integrally formed with the shaft.

A43. The reamer device of any of paragraphs A1-A42, wherein the cutter head portion is not removable from the shaft without destruction or damage to the reamer device.

A44. The reamer device of any of paragraphs A1-A43, wherein the reamer device is configured such that the cutter head portion is coupled to the shaft and in a cutting position when a/the guide pin is received within the interior cannula track, wherein the cutter head portion is positioned to cut the patient's bone in the cutting position.

A45. The reamer device of any of paragraphs A1-A44, further comprising a sliding ring that is configured to engage the outer surface of the shaft and the slot, wherein the sliding ring is configured to slide longitudinally with respect to the shaft and the slot, and wherein the sliding ring is configured to capture a/the guide pin within the interior cannula track such that the guide pin is not prematurely removed from the shaft once received within the interior cannula track.

A46. The reamer device of paragraph A45, further comprising a guide handle tool that is configured to move the sliding ring relative to the shaft and the slot.

A46.1. The reamer device of paragraph A46, wherein the guide handle tool is configured to secure the sliding ring in a selected position relative to the shaft and the slot.

A47. The reamer device of any of paragraphs A45-A46.1, wherein the sliding ring is configured to be selectively positioned with respect to the shaft after a/the guide pin is received within the interior cannula track.

A48. The reamer device of any of paragraphs A1-A47, wherein the reamer device is configured to be used on a plurality of different patients, such that the reamer device is not an example of patient-specific instrumentation.

A49. The reamer device of any of paragraphs A1-A48, wherein the reamer device is configured to be sterilizable and reusable.

A50. The reamer device of any of paragraphs A1-A49, further comprising one or more anti-rotation features configured to prevent rotation of the cutter head portion with respect to the shaft.

A51. The reamer device of paragraph A50, wherein the one or more anti-rotation features comprise threads, splines, and/or a non-circular cross-sectional area.

B1. A system for preparing a patient's bone for receiving an implant component, comprising:
the reamer device of any of paragraphs A1-A51; and
a guide pin extending from a leading end to a trailing end, wherein the leading end is configured to be inserted partially into the patient's bone that the reamer device is configured to cut, the guide pin being configured to assist in alignment and positioning of the reamer device with respect to the patient's bone.

B2. The system of paragraph B1, wherein the guide pin comprises an/the enlarged guide pin portion.

B3. The system of paragraph B2, wherein the guide pin comprises a smaller guide pin portion.

B4. The system of paragraph B3, wherein a first diameter of the enlarged guide pin portion is greater than a second diameter of the smaller guide pin portion.

B5. The system of any of paragraphs B3-B4, wherein the enlarged guide pin portion is configured to cooperate with the reamer device such that the enlarged guide pin portion functions as a depth guide such that it limits the extent to which the reamer device may be inserted onto the guide pin.

B6. The system of any of paragraphs B3-B5, wherein the enlarged guide pin portion is positioned at or near the leading end of the guide pin.

B7. The system of any of paragraphs B3-B6, wherein the smaller guide pin portion extends from the enlarged guide pin portion to or near the trailing end of the guide pin.

B8. The system of any of paragraphs B3-B7, wherein the enlarged guide pin portion is configured to engage a/the step formed within the interior cannula track of the reamer device.

B9. The system of any of paragraphs B3-B8, wherein the enlarged guide pin portion is configured to be positioned within an/the enlarged inner diameter portion of the interior cannula track of the reamer device.

B10. The system of any of paragraphs B3-B9, wherein the smaller guide pin portion is configured to be positioned within an/the reduced inner diameter portion of the interior cannula track of the reamer device.

B11. The system of any of paragraphs B4-B10, when depending from B4, wherein an/the opening width of the slot of the reamer device is smaller than the first diameter of the enlarged guide pin portion.

B12. The system of any of paragraphs B4-B11, when depending from B4, wherein an/the opening width of the slot of the reamer device is greater than the second diameter of the smaller guide pin portion.

B13. The system of any of paragraphs B1-B12, wherein the system is configured such that the reamer device is engaged with the guide pin at a location within the patient's body that is between the patient's humeral head, and an/the enlarged guide pin portion of the guide pin.

B14. The system of any of paragraphs B1-B13, wherein when the guide pin is inserted into the patient's bone, an/the enlarged guide pin portion of the guide pin extends laterally from the patient's glenoid surface, but ends medial to the patient's humeral head.

B15. The system of any of paragraphs B1-B14, wherein the guide pin comprises a plurality of graduated markings configured for gauging the extent to which the reamer device has been inserted onto the guide pin.

B16. The system of paragraph B15, wherein the plurality of graduated markings are positioned on a/the enlarged guide pin portion.

B17. The system of any of paragraphs B1-B16, wherein the guide pin has a guide pin length that extends sufficiently for accurate insertion of the guide pin into the shaft of the reamer device.

B18. The system of any of paragraphs B1-B17, wherein a first length of an/the enlarged guide pin portion is sized relative to the geometry of the cutter head portion of the reamer device to allow space to engage the cutter head portion with the guide pin at a location within the patient's body that is medial to the patient's humeral head.

B19. The system of any of paragraphs B1-B8, further comprising one or more of a drill chuck, a quick connect guide, and a drive shaft configured to couple the reamer device to a drill and cause rotation of the cutter head portion to cut the patient's bone.

B20. The system of paragraph B19, wherein the reamer device comprises a threaded portion on or in the shaft for selectively operatively coupling the reamer device to the one or more of the drill chuck, the quick connect guide, and the drive shaft.

B21. The system of paragraph B20, wherein the threaded portion comprises reverse threads positioned at or near the proximal end of the shaft.

C1. A method for performing shoulder surgery, comprising:
providing the reamer device of any of paragraphs A1-A51 and/or the system of any of paragraphs B1-B21;
engaging the reamer device with a/the guide pin by moving the shaft with respect to the guide pin such that the guide pin passes radially through the slot formed in the outer surface of the shaft and is received within the interior cannula track of the shaft; and
capturing the guide pin within the shaft.

C1.1. The method of paragraph C1, further comprising inserting the guide pin into a patient's glenoid, wherein the engaging the reamer device with the guide pin is performed at a location medial to the patient's humeral head.

C2. The method of paragraph C1 or C1.1, further comprising cutting the patient's glenoid with the cutter head portion of the reamer device.

C3. The method of any of paragraphs C1-C2, further comprising operatively coupling the reamer device to a drive shaft configured to rotate the cutter head portion of the reamer device relative to the patient's glenoid, thereby removing some of the patient's bone and preparing the glenoid for receiving an implant component during shoulder surgery.

C4. The method of any of paragraphs C1-C3, wherein the capturing the guide pin within the shaft comprises pivoting the shaft with respect to the guide pin such that the guide pin is received within the interior cannula track and such that the guide pin is prevented from being prematurely removed from the slot of the reamer device.

C5. The method of any of paragraphs C1-C4, wherein the capturing the guide pin within the shaft comprises positioning a/the sliding ring onto the shaft such that it engages the slot and the outer surface of the shaft, and such that it prevents premature removal of the guide pin from the slot of the reamer device.

C6. The method of any of paragraphs C1-05, further comprising longitudinally sliding the shaft with respect to the guide pin, wherein the longitudinally sliding is performed after the engaging the reamer device with the guide pin.

C7. The method of any of paragraphs C1-C6, wherein the engaging the reamer device with the guide pin comprises moving the reamer device laterally and/or posteriorly with respect to the guide pin such that the shaft is positioned onto a/the smaller guide pin portion of the guide pin, wherein a/the enlarged guide pin portion is positioned distal to the smaller guide pin portion.

C8. The method of paragraph C7, further comprising moving the reamer device longitudinally with respect to the guide pin until a/the step formed within the interior cannula track engages the enlarged guide pin portion.

C9. The method of any of paragraphs C1-C8, wherein the cutter head portion is a selectively detachable cutter head portion, and wherein the method further comprises coupling the selectively detachable cutter head portion to the shaft within a/the patient's shoulder cavity.

C10. The method of any of paragraphs C1-C9, wherein the engaging the reamer device with the guide pin comprises inserting the reamer device eccentrically.

C11. The method of any of paragraphs C1-C10, wherein the engaging the reamer device with the guide pin comprises aligning the slot of the reamer device with the guide pin.

C12. The method of any of paragraphs C1.1-C11, when depending from C1.1, wherein the inserting the guide pin into the patient's glenoid comprises inserting the guide pin at a predetermined depth within the patient's glenoid.

C13. The method of any of paragraphs C1-C12, further comprising coupling a/the drill chuck or drive shaft to the proximal end of the shaft of the reamer device.

C14. The method of any of paragraphs C1-C13, comprising avoiding bending of the guide pin while engaging the reamer device with the guide pin and capturing the guide pin within the shaft.

D1. A method, comprising:

providing the reamer device of any of paragraphs A1-A51 and/or the system of any of paragraphs B1-B21;

placing the cutter head portion of the reamer device in proximity to a/the guide pin inserted within a/the patient's glenoid such that the shaft of the reamer device is positioned at a non-parallel angle with respect to the guide pin;

aligning the slot of the reamer device with the guide pin;

moving the cutter head portion towards the guide pin such that a/the portion of the slot formed in the cutter head portion is moved onto the guide pin; and pivoting the shaft towards the guide pin until the guide pin and the shaft are substantially parallel with one another, and such that the guide pin passes through the slot and is received within the interior cannula track.

D2. The method of paragraph D1, further comprising any of the steps of paragraphs C1-C14.

The various elements of reamer devices and systems disclosed herein are not required to all reamer devices and systems according to the present disclosure, and the present disclosure includes all novel and non-obvious combinations and subcombinations of the various elements disclosed herein. Moreover, one or more of the various elements disclosed herein may define independent inventive subject matter that is separate and apart from the whole of a disclosed reamer device or system. Accordingly, such inventive subject matter is not required to be associated with the specific reamer devices and systems that are expressly disclosed herein, and such inventive subject matter may find utility in reamer devices and systems that are not expressly disclosed herein.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. A reamer device configured to prepare a patient's glenoid for shoulder arthroplasty, comprising:

a shaft extending from a proximal end to a distal end, the shaft comprising:

an inner surface defining an interior cannula track, wherein the shaft is configured to receive a guide pin within the interior cannula track such that the guide pin is substantially parallel with the interior cannula track when received in the interior cannula track, and wherein the shaft is configured to slide longitudinally with respect to the guide pin when the guide pin is positioned within the interior cannula track;

an outer surface opposite the inner surface; and a slot formed in the outer surface of the shaft, wherein the slot extends longitudinally along the shaft from the distal end of the shaft towards the proximal end of the shaft, wherein the slot extends radially from the outer surface of the shaft to the interior cannula track, wherein the reamer device is configured to receive the guide pin within the interior cannula track by passing the guide pin through the slot, wherein the slot extends longitudinally between a proximal slot end and a distal slot end, wherein the proximal slot end is configured to selectively capture a portion of the guide pin within the interior cannula track, and wherein the shaft is configured such that the reamer device is not prematurely removed from the guide pin once the guide pin is received within the interior cannula track; and a cutter head portion positioned at the distal end of the shaft, the cutter head portion being configured to cut a patient's glenoid, wherein the interior cannula track and the slot extend through the cutter head portion.

2. The reamer device according to claim 1, wherein the shaft is configured such that it may be placed onto the guide pin by lateral movement of the shaft and the cutter head portion with respect to the guide pin.

3. The reamer device according to claim 1, wherein the shaft is configured to engage the guide pin by placing the cutter head portion in proximity to the guide pin such that the shaft is positioned at a non-parallel angle with respect to the guide pin, aligning the slot with the guide pin, moving the cutter head portion towards the guide pin such that a portion of the slot formed in the cutter head portion is placed onto the guide pin, and pivoting the shaft towards the guide pin until the guide pin and the shaft are substantially parallel and the guide pin passes through the slot and is received within the interior cannula track.

4. The reamer device according to claim 1, wherein the interior cannula track comprises an enlarged inner diameter portion and a reduced inner diameter portion, wherein the enlarged inner diameter portion has an enlarged inner diameter that is greater than a reduced inner diameter of the reduced inner diameter portion of the interior cannula track, wherein the enlarged inner diameter portion is adjacent the cutter head portion, and wherein the enlarged inner diameter portion extends longitudinally from the distal end of the shaft towards the proximal end of the shaft.

5. The reamer device according to claim 4, wherein the interior cannula track comprises a step formed at an interface of the enlarged inner diameter portion and the reduced inner diameter portion.

6. The reamer device according to claim 1, wherein the shaft further comprises a finger relief configured to allow pressure to be applied to the guide pin at a location radially inward from the outer surface of the shaft while the guide pin is being positioned within the interior cannula track, wherein the finger relief is configured to allow a user to push the guide pin into the interior cannula track.

7. The reamer device according to claim 1, wherein the slot has an opening width that is smaller than an enlarged guide pin portion of the guide pin on which the interior cannula track is configured to be positioned.

8. The reamer device according to claim 1, wherein the slot comprises a medial slot and a lateral slot opposite the medial slot, wherein one of the medial slot and the lateral slot is positioned adjacent the cutter head portion, and wherein the other of the medial slot and the lateral slot is positioned closer to the proximal end of the shaft.

9. The reamer device according to claim 1, wherein the cutter head portion is integrally formed with the shaft.

10. A system for preparing a patient's bone for receiving an implant component, comprising:
the reamer device according to claim 1; and
the guide pin, wherein the guide pin extends from a leading end to a trailing end, wherein the leading end is configured to be inserted partially into the patient's bone that the reamer device is configured to cut, the guide pin being configured to assist in alignment and positioning of the reamer device with respect to the patient's bone, the guide pin further comprising:
an enlarged guide pin portion; and
a smaller guide pin portion, wherein a first diameter of the enlarged guide pin portion is greater than a second diameter of the smaller guide pin portion, wherein the enlarged guide pin portion is configured to cooperate with the reamer device such that the enlarged guide pin portion functions as a depth guide such that it limits the extent to which the reamer device may be inserted onto the guide pin.

11. The system according to claim 10, wherein the enlarged guide pin portion is configured to engage a step formed between an enlarged inner diameter portion and a reduced inner diameter portion within the interior cannula track of the reamer device, wherein the enlarged guide pin portion is configured to be positioned within the enlarged inner diameter portion of the interior cannula track of the reamer device, and wherein the smaller guide pin portion is configured to be positioned within the reduced inner diameter portion of the interior cannula track of the reamer device.

12. The system according to claim 10, wherein an opening width of the slot of the reamer device is smaller than the first diameter of the enlarged guide pin portion, and wherein the opening width of the slot of the reamer device is greater than the second diameter of the smaller guide pin portion.

13. The system according to claim 10, wherein the system is configured such that the reamer device is engaged with the guide pin at a location within the patient's body that is between the patient's humeral head and the enlarged guide pin portion of the guide pin.

14. The system according to claim 10, wherein a first length of the enlarged guide pin portion is sized relative to the geometry of the cutter head portion of the reamer device to allow space to engage the cutter head portion with the guide pin at a location within the patient's body that is medial to the patient's humeral head.

15. The system according to claim 10, further comprising one or more of a drill chuck, a quick connect guide, and a drive shaft configured to couple the reamer device to a drill and cause rotation of the cutter head portion to cut the patient's bone; wherein the reamer device comprises a threaded portion on or in the shaft for selectively operatively coupling the reamer device to the one or more of the drill chuck, the quick connect guide, and the drive shaft.

16. A method for performing shoulder surgery, comprising:
providing the system of claim 10;
inserting the guide pin into a patient's glenoid;
engaging the reamer device with the guide pin by moving the shaft with respect to the guide pin such that the guide pin passes radially through the slot formed in the outer surface of the shaft and is received within the interior cannula track of the shaft, wherein the engaging the reamer device with the guide pin is performed at a location medial to the patient's humeral head; and
capturing the guide pin within the shaft.

17. A method, comprising:
providing the system of claim 10;
placing the cutter head portion of the reamer device in proximity to the guide pin inserted within a patient's glenoid such that the shaft of the reamer device is positioned at a non-parallel angle with respect to the guide pin;
aligning the slot of the reamer device with the guide pin;
moving the cutter head portion towards the guide pin such that a portion of the slot formed in the cutter head portion is moved onto the guide pin; and
pivoting the shaft towards the guide pin until the guide pin and the shaft are substantially parallel with one another, and such that the guide pin passes through the slot and is received within the interior cannula track of the reamer device.

18. A reamer device configured to prepare a patient's glenoid for shoulder arthroplasty, comprising:
a shaft extending from a proximal end to a distal end, the shaft comprising:
an inner surface defining an interior cannula track, wherein the shaft is configured to receive a guide pin within the interior cannula track such that the guide pin is substantially parallel with the interior cannula track when received in the interior cannula track, and wherein the shaft is configured to slide longitudinally with respect to the guide pin when the guide pin is positioned within the interior cannula track;
an outer surface opposite the inner surface; and
a slot formed in the outer surface of the shaft, wherein the slot extends longitudinally along the shaft from the distal end of the shaft towards the proximal end of the shaft, wherein the slot extends radially from the outer surface of the shaft to the interior cannula track; and wherein the reamer device is configured to receive the guide pin within the interior cannula track by passing the guide pin through the slot;
a cutter head portion positioned at the distal end of the shaft, the cutter head portion being configured to cut a patient's glenoid, wherein the interior cannula track and the slot extend through the cutter head portion; and
a sliding ring that is configured to engage the outer surface of the shaft and the slot, wherein the sliding ring is configured to slide longitudinally with respect to the shaft and the slot, wherein the sliding ring is configured to capture the guide pin within the interior cannula track such that the guide pin is not prematurely removed from the shaft once received within the interior cannula track, and wherein the sliding ring is configured to be selectively positioned with respect to the shaft after the guide pin is received within the interior cannula track.

19. The reamer device according to claim 18, further comprising a guide handle tool that is configured to move the sliding ring relative to the shaft and the slot.

20. The reamer device according to claim 19, wherein the guide handle tool is configured to secure the sliding ring in a selected position relative to the shaft and the slot.

* * * * *